(12) United States Patent
Dahlin et al.

(10) Patent No.: US 10,034,978 B2
(45) Date of Patent: Jul. 31, 2018

(54) METHOD AND SYSTEM FOR DOSE RATE REGULATION IN DRUG INFUSION TREATMENT

(71) Applicant: PHARMACOLOG I UPPSALA AB, Uppsala (SE)

(72) Inventors: Hans Dahlin, Bjorklinge (SE); Jorgen Hojdmo, Uppsala (SE)

(73) Assignee: PHARMACOLOG I UPPSALA AB, Uppsala (SE)

( * ) Notice: Subject to any disclaimer, the term of this patent is extended or adjusted under 35 U.S.C. 154(b) by 0 days.

(21) Appl. No.: 15/546,911

(22) PCT Filed: Jan. 26, 2016

(86) PCT No.: PCT/SE2016/050049
§ 371 (c)(1),
(2) Date: Jul. 27, 2017

(87) PCT Pub. No.: WO2016/122382
PCT Pub. Date: Aug. 4, 2016

(65) Prior Publication Data
US 2018/0028750 A1 Feb. 1, 2018

(30) Foreign Application Priority Data
Jan. 27, 2015 (SE) ...................... 1550082

(51) Int. Cl.
*G01J 3/00* (2006.01)
*A61M 5/168* (2006.01)
(Continued)

(52) U.S. Cl.
CPC .... *A61M 5/16877* (2013.01); *A61M 5/14228* (2013.01); *A61M 5/14546* (2013.01);
(Continued)

(58) Field of Classification Search
CPC ...... A61M 5/168; A61M 5/145; A61M 5/142; G06F 19/00; G01J 3/02; G01J 3/42; G01N 21/31; G01N 21/05
See application file for complete search history.

(56) References Cited

U.S. PATENT DOCUMENTS

| 4,634,426 A | 1/1987 | Kamen |
| 6,111,639 A | 8/2000 | Reduto |
(Continued)

FOREIGN PATENT DOCUMENTS

| WO | 01/83007 A2 | 11/2001 |
| WO | 2004/033003 A1 | 4/2004 |
(Continued)

OTHER PUBLICATIONS

International Search Report, dated Apr. 22, 2016, from corresponding PCT application No. PCT/SE2016/050049.

*Primary Examiner* — Abdullahi Nur
(74) *Attorney, Agent, or Firm* — Young & Thompson

(57) ABSTRACT

A system for drug delivery by infusion is disclosed where the concentration of the drug solution withdrawn from a drug container (1, 2) to be delivered to the patient (8) according to a predetermined dose rate protocol for the drug is repeatedly analyzed during the infusion, and the concentration data obtained are used to continuously control the infusion rate to at least substantially maintain the predetermined dose rate. A method for drug delivery by infusion is also disclosed.

20 Claims, 3 Drawing Sheets

(51) Int. Cl.
  *A61M 5/172*   (2006.01)
  *A61M 5/145*   (2006.01)
  *A61M 5/142*   (2006.01)
  *G06F 19/00*   (2018.01)

(52) U.S. Cl.
  CPC ......... *A61M 5/172* (2013.01); *G06F 19/3468* (2013.01); *A61M 2005/14208* (2013.01); *A61M 2205/3306* (2013.01); *A61M 2205/3379* (2013.01); *A61M 2205/50* (2013.01); *A61M 2205/52* (2013.01); *A61M 2205/6009* (2013.01)

(56) References Cited

U.S. PATENT DOCUMENTS

| | | |
|---|---|---|
| 2003/0204330 A1 | 10/2003 | Allgeyer |
| 2004/0077997 A1 | 4/2004 | Jasperson et al. |
| 2010/0305499 A1 | 12/2010 | Matsiev et al. |
| 2014/0111801 A1 | 4/2014 | Cohen |
| 2015/0045641 A1* | 2/2015 | Rule .................. A61B 5/7435 600/347 |

FOREIGN PATENT DOCUMENTS

| | | |
|---|---|---|
| WO | 2004/109262 A1 | 12/2004 |
| WO | 2009/114115 A1 | 9/2009 |
| WO | 2014/164809 A1 | 10/2014 |

* cited by examiner

METHOD AND SYSTEM FOR DOSE RATE REGULATION IN DRUG INFUSION TREATMENT

FIELD OF THE INVENTION

The present invention relates to the administration of drugs by infusion, and more particularly to a method and a system for infusion of a drug-containing liquid involving fluid analysis of the identity and concentration of the drug or drugs that are to be administered.

BACKGROUND OF THE INVENTION

Delivery of the correct medication, dose and volume at the appropriate infusion rate and time is essential for safe administration of medication by infusion, generally intravenously.

Drug solutions for administration by infusion are provided in various ways. Certain drug solutions, such as cytostatic drugs, are prepared at hospital pharmacies or at drug manufacturers, whereas other drugs, such as antibiotics and morphine, are prepared at hospital pharmacies or at the wards, either from a base solution or a powder formulation.

While the hospital routines are rigorous, the risk for mistakes by pharmacy and hospital personnel cannot be totally avoided. Not only can mistakes be made in the manual preparation of a drug solution, but for example mix-up of different medicaments may also take place at the moment when the drug container is connected to the device used for the administration. Since drugs for infusion are often highly potent, errors in drug composition and concentration may have serious effects on the patient and can even be fatal.

To eliminate the consequences of such mistakes devices have been proposed which immediately before infusion analysis whether the administration container set up for infusion contains the correct drug or not, and if the concentration of the drug solution is as prescribed.

WO 2004/109262 A1 discloses a method and a device to perform verification of the identity of a drug in an administration container by loading drug from the container to an analyzing unit, non-invasively determining a value of at least one chemical and/or physical property of a drug solution to generate a profile for the drug, and comparing the obtained profile with a set of known profiles. If agreement between the obtained profile and the profile of the prescribed drug is reached a message is issued that the treatment is safe and administration of the drug can proceed. Optionally, also the concentration of the drug is verified before the administration is allowed to proceed. The non-invasive analysis is preferably performed by absorption spectrophotometry.

A similar approach is disclosed in WO 2004/033003 A1, where a device and process for preventing medical errors due to the improper administration of an intravenously delivered medication include spectroscopic analysis of intravenous fluid components. An emission source and a detector are placed adjacent to the intravenous tubing of an administration set to generate signals for spectroscopic analysis. The signals are processed to identify the medication and preferably also the concentration of the medication. In a preferred embodiment, the emission source, detector and hardware and software for the spectroscopic analysis are placed in an infusion pump.

In the devices and processes outlined above, failure to verify the identity of the drug in the drug administration container results in disposal of the container and replacement with a new drug container. Disposal of the drug container would also be the result if the concentration of the drug is determined and is found not to correspond to or to unacceptably deviate from the label concentration.

It is an object of the present invention to provide means for proceeding with the administration of the drug solution even if the determined concentration is not the correct one or is within an acceptable range.

As is well known, drug molecules may adhere to the inner wall of the drug container, such as an infusion bag, which may result in an inhomogeneous drug solution within the container which in turn may result in a varying drug concentration of the drug solution administered to the patient, even if the container has been gently shaken or massaged before the set up. A varying drug concentration may also be due the drug solution undergoing a change during the infusion process.

It is another object of the present invention to deliver a correct dosage of a drug administered by infusion even if the concentration of the administered drug solution varies during the infusion.

It is another object of the present invention to provide a method and a system capable of identifying the drug and the concentration by means of spectrophotometry.

SUMMARY OF THE INVENTION

According to the present invention, the above-mentioned objects and other advantages are obtained by providing a drug delivery system where the concentration of the drug solution withdrawn from the drug container to be delivered to the patient according to a predetermined (prescribed) dose rate protocol for the drug is repeatedly analyzed during the infusion, and the concentration data obtained are used to continuously control the infusion rate to at least substantially maintain the predetermined dose rate.

In one aspect, the present invention provides a system for administering a drug solution by infusion. The system comprising a drug container containing a label drug solution with a label concentration of a drug, a drug delivery set comprising a fluid conduit connected to the drug container means for connecting the fluid conduit to a patient. The system further comprises a detection chamber in the fluid conduit between the drug container and the patient connection means, and adjustment means for setting an infusion rate corresponding to a predetermined dose rate of the drug based on the label concentration. The system further comprises analytical detection means for non-invasive determination in the detection chamber of the identity and concentration of the drug in fluid withdrawn from the drug container into to the fluid conduit, and means for preventing infusion of drug solution from the drug container if the label drug is not identified. The system further comprises a control unit comprising a processor and a memory said memory containing instructions executable by said processor whereby said processor is operative to providing spectrophotometric reference curves with different concentrations of the label drug to be identified, performing a spectrophotometric measurement of the drug solution by means of the analytical detection means, wherein a measured spectrophotometric curve is obtained, finding two consecutive spectrophotometric reference curves from the provided spectrophotometric reference curves, such that the two consecutive spectrophotometric reference curves encompasses the measured spectrophotometric curve of the drug solution in a defined wavelength region. The processor is further operative to determine the intensity of the measured spectrophotometric curve at a first wavelength, and for calculating a calculated spectrophotometric curve of the fluid by means of the determined intensity at the first wavelength and by using Beer-Lamberts law and the two consecutive spectrophotometric reference curves. The processor is further operative to determine if a difference between the calculated spectrophotometric curve and the measured spectrophotometric curve is smaller than a predetermined threshold, and upon determining that the difference is smaller than the predetermined threshold, the drug is identified to be equal to the drug of the two consecutive reference curves, which is the label drug, and the concentration of the drug in the fluid is equal to the concentration of the drug in the calculated spectrophotometric curve. The processor is further operative to control the adjustment means and to calculate and set the adjustment means to an adjusted infusion rate in order to maintain the predetermined dose rate when the drug concentration determined in the detection chamber deviates from the label concentration of the drug.

In another aspect, the present invention provides a method of administering a drug solution by infusion. The method comprising providing a drug container with a label drug solution containing a label concentration of the drug, coupling the drug container to a drug delivery set for administration of drug solution to a patient by infusion via a fluid path, wherein the fluid path contains a detection chamber, based on the label concentration of the drug in the drug container, setting an infusion rate for the drug delivery set corresponding to a predetermined dose rate of the drug. The method further comprising withdrawing drug solution from the drug container through the detection chamber and non-invasively determining the identity and concentration of the drug in the detection chamber. The method further comprising providing spectrophotometric reference curves with different concentrations for the label drug to be identified. The method further comprising performing a spectrophotometric measurement of the drug solution by means of the analytical detection means, wherein a measured spectrophotometric curve is obtained. The method comprises finding two consecutive spectrophotometric reference curves from the provided spectrophotometric reference curves, such that the two consecutive spectrophotometric reference curves encompasses the measured spectrophotometric curve of the drug solution in a defined wavelength region.

The method further comprises determining the intensity of the measured spectrophotometric curve at a first wavelength. The method further comprises calculating a calculated spectrophotometric curve of the fluid by means of the determining intensity at the first wavelength and by using Beer-Lamberts law and the two consecutive spectrophotometric reference curves. The method further comprises determining if a difference between the calculated spectrophotometric curve and the measured spectrophotometric curve is smaller than a predetermined threshold, and upon determining that the difference is smaller than the predetermined threshold, the drug is identified to be equal to the drug of the two consecutive reference curves, which is the label drug, and a concentration of the drug in the fluid is equal to the concentration of the drug in the calculated spectrophotometric curve. The method further comprises control the adjustment means and to calculate and set the adjustment means to an adjusted infusion rate in order to maintain the predetermined dose rate when the drug concentration determined in the detection chamber deviates from the label concentration of the drug. If the label drug is identified, and the determined drug concentration corresponds to the label concentration, permitting infusion of the drug solution at the set infusion rate, and if the label drug is not identified, preventing infusion of drug solution. If the label drug is identified but the determined drug concentration does not correspond to the label drug concentration, calculating and setting an adjusted infusion rate for the drug delivery set which at least substantially will maintain the predetermined dose rate of the drug, and permitting infusion of the drug solution at the adjusted infusion rate.

The terms "label drug" and "label concentration" as used herein are to be interpreted in a broad sense and do not necessarily refer a label on the drug container but also includes information on the identity and concentration, respectively, of the specific drug provided in any other way.

The terms "predetermined infusion rate" and "predetermined dose rate" as used herein refer to a predetermined infusion rate and dose rate, respectively, which can either be fixed or varied in a predetermined manner.

In one embodiment of the method and the system, the first wavelength is a wavelength wherein a difference between the two consecutive spectrophotometric reference curves is maximal. This way a good resolution of the intensity in the spectrophotometric curve is attainable.

In one embodiment of the method and the system, upon determining that the difference is larger than the predetermined threshold, adjust the selected concentration, and calculate the spectrophotometric curve using the adjusted selected concentration. This way the difference may be minimized and thereby a better fit of the calculated spectrophotometric curve to the measured spectrophotometric curve is achieved.

In one embodiment of the method and the system, the determination of the drug concentration is performed repeatedly at a plurality of times during the infusion process, an adjusted infusion rate being calculated and set each time based on the momentarily determined concentration as well as the cumulated infused dose of the drug. In this way, the desired (prescribed) total dose of the drug will be administered if the infusion is performed during the infusion time length corresponding to that set for the label drug concentration and the desired dose rate of the drug.

In one embodiment, the drug delivery set comprises an infusion pump, typically a peristaltic pump or a syringe pump, which comprises the adjustment means controlled by the control unit.

In one embodiment, the detection chamber, and optionally also the analytical detection means and (partially or wholly) the control unit, are provided in the infusion pump.

In one embodiment, the predetermined dose rate of the drug is varied in a predetermined manner with different fixed dose rates delivered at different intervals, such as, for example, delivering a higher dose rate for an initial period of the infusion time, and a lower dose rate for the remaining infusion time, or vice versa.

A more complete understanding of the invention, as well as further features and advantages thereof, will be obtained by reference to the following detailed description and drawing.

DETAILED DESCRIPTION OF THE INVENTION

The following description is for illustration and exemplification of the invention only and is not intended to limit the invention to the specific embodiments described. All references cited herein, including patents and patent applications, are incorporated by reference in their entirety. Unless defined otherwise, technical and scientific terms have the same meaning as commonly understood by one of ordinary skill in the art to which this invention belongs. The meanings of the terms dose, infusion rate, dose rate, and spectrophotometric curves as used herein are as follows.

The "dose" of a drug is the amount of drug intended for infusion over a specific length of time, e.g. in mg.

The "infusion rate" (or flow rate) is the liquid volume infused per time unit, e.g. mL/minute, determining how rapidly the infusion is delivered to the patient.

The "dose rate" is the amount of drug delivered per time unit, e.g. mg per minute, and is determined by the concentration of the drug and the infusion rate.

The "spectrophotometric curve" is a set of data points, wherein each data point is a spectrophotometric variable at a specific wavelength of light. For example in a preferred embodiment the spectrophotometric parameter is the absorbance of light. But other spectrophotometric variable such as reflectance is of course also possible.

Figure 1:
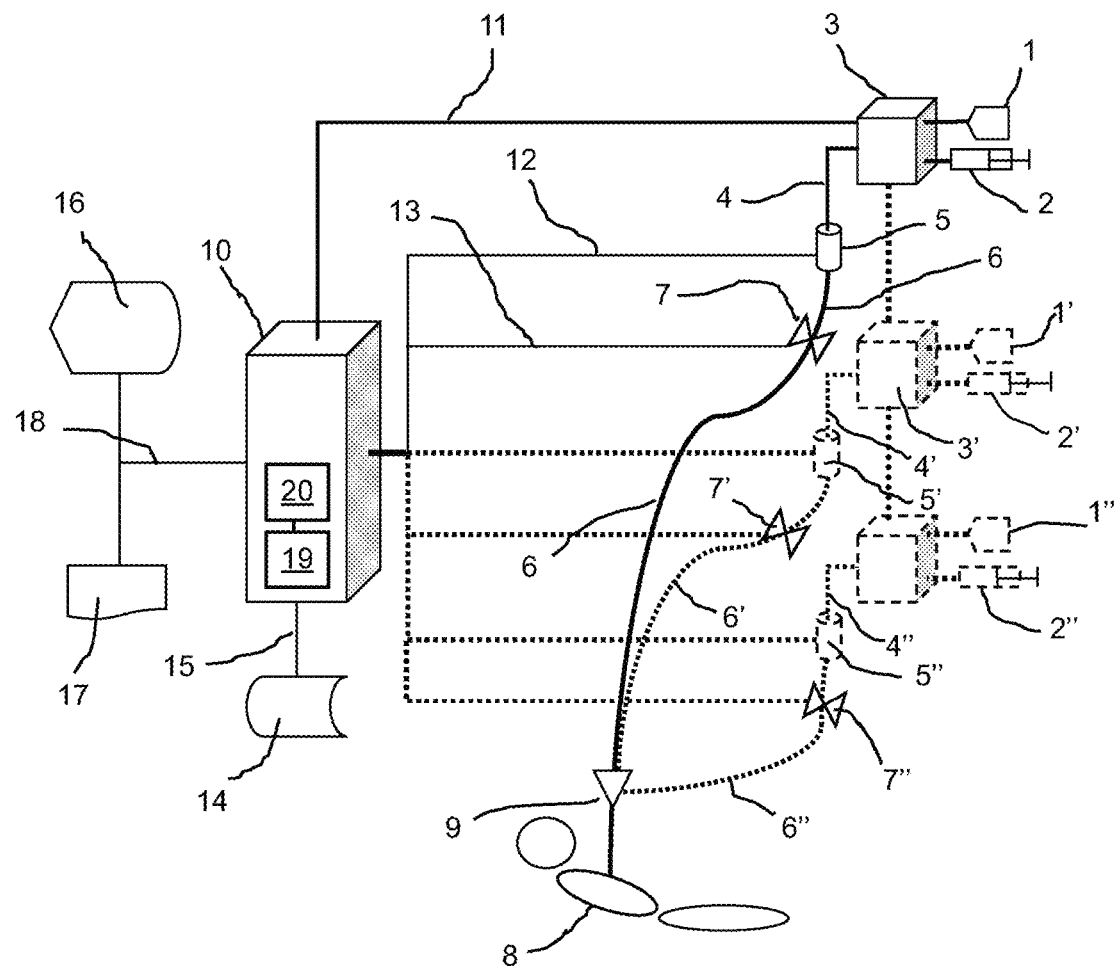
FIG. 1 is a schematic view of an embodiment of a system for drug infusion according to the present invention.

As mentioned above, the present invention relates to a method and system for safe delivery of a drug by infusion, wherein the identity of the drug in a drug container set up for the infusion is verified, and the concentration of the drug is repeatedly measured during the infusion and the infusion rate adjusted when necessary to maintain a desired or prescribed average dose rate for the drug. Such a system for intravenous infusion is schematically illustrated in FIG. 1.

A drug container, here exemplified by a bag 1 or a syringe 2, is connected to a flow pump 3, which when the container is an infusion bag typically may be a peristaltic pump, and in case of a syringe, a syringe pump.

The pump 3 is via a first tubing part 4 connected to a detection chamber, here not visible being concealed by a surrounding analytical detection unit 5 for non-invasive detection of drug solution. The latter is in turn via a second tubing part 6 containing a control valve 7 connected to a patient 8 through e.g. a hypodermic needle or peripheral cannula (not shown).

While the detection chamber provided between the tubing parts 4 and 6, depending on the detection system used, may be a defined portion of a single tubing comprising the parts 4 and 6, the chamber typically has a defined width and is optically transparent to provide an "optical window" for spectroscopic analysis, e.g. of the "closed cuvette" type. Such analysis may be based on measuring radiation that is transmitted, adsorbed or reflected by the fluid in the detection chamber, depending on the type of spectroscopic system. Optionally, the detection chamber may be arranged in the flow pump 3, e.g. as described in the aforementioned WO 2004/033003 A1.

Figure 2:
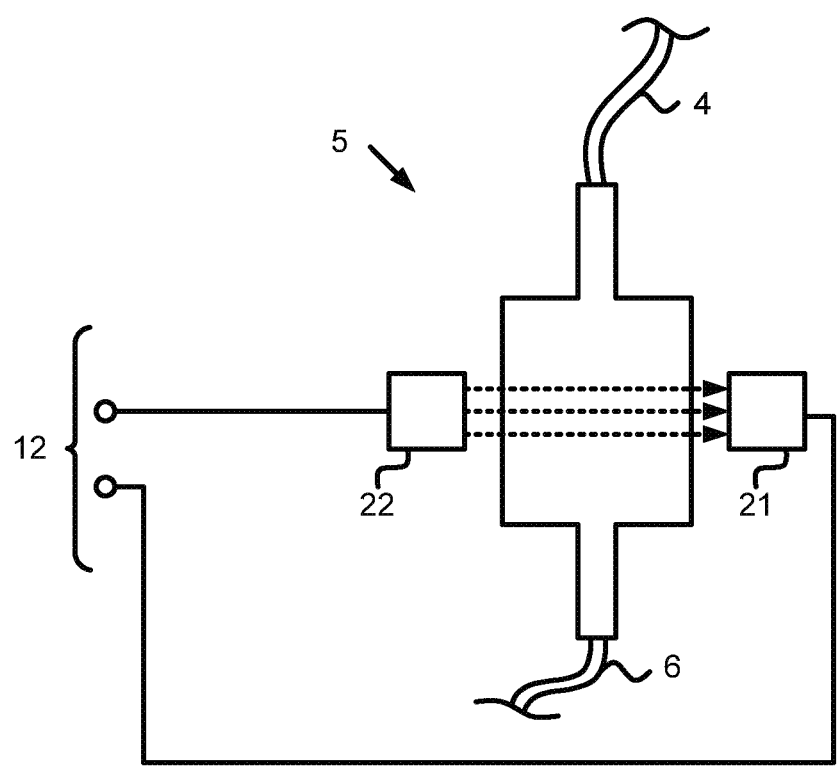
FIG. 2 is a schematic view of an embodiment of an analytical detection unit.

Now with reference made to FIG. 2 a preferred analytical detection unit 5 will be disclosed. This preferred analytical detection unit 5 comprises a spectrophotometric measuring setup, comprising a light source 21 and a photodetector. The light source 22 is configured to transmit light through the detection chamber, here designated 23. The photodetector is configured to receive the light transmitted through the detection chamber and to send a signal comprising light absorbance for a plurality of wavelengths. A preferred spectrophotometric setup provides 1024 measuring channels i.e. bins that the wavelength region of interest is mapped onto. This way the signal contains detailed absorbance data for each bin that forms the wavelength spectra of interest.

Now with reference made to FIG. 1 again, the detection chamber comprises a short cylinder of quartz or UV-transparent plastic, such as Topas™ (a cyclic olefin polymer) with Luer fittings cooperating with Luer fittings on the tubing parts 4 and 6.

Exemplary analytical techniques permitting measurements of both the identity and concentration of a drug component in an infusion liquid include fluorescence spectrophotometry and Raman spectroscopy. Optionally, the analytical detection unit includes dual measurement devices, one for the molecular verification and one for the concentration measurements. Analytical techniques for molecular verification additionally include, e.g. NMR and ESR. For a more detailed description of optical measurements in infusion devices it may be referred to the aforementioned WO 2004/109262 A1 and WO 2004/033003 A1.

The pump 3 is connected to a control unit (or controller) 10, typically a computer comprising a memory 19 and a processor 20, through a line 11. To the control unit 10 are further connected the analytical detection unit 5 through a transfer line 12, and the control valve 7 through a line 13. In the illustrated case, the control unit 10 is also connected to a calibration data storage (or memory) 14, which may e.g. also contain patient treatment protocol as well as other data, through a line 15, and to an operation control display 16 and a printer 17, respectively, through a line 18.

In one preferred embodiment the calibration data storage 14 comprises reference spectrophotometric curves for drugs of interest. This data is available to the processor through line 15. The calibration data storage may be a remote server or a cloud service available through internet. In other embodiments it may be a hard disc, or a removable memory such as a USB thumb drive, connected to the control unit 10.

Indicated by dashed contours are two additional sets of drug container, pump and analytical detection unit connected to the patient and the control unit via dotted tubing parts and lines, identical components being indicated by primed and double-primed numerals, respectively.

While the drug, or pharmaceutical, may be any drug given to a patient through infusion, an important application of the present invention is the verification of drug liquids used for chemotherapy of cancer, where the prescription is tailored for each patient and any errors in the type of drug and its concentration may have very serious and even lethal effects on the patient.

An appropriate order for intravenous infusion to a specific patient typically specifies the dose of the drug in question to be given over a specific interval and the concentration of the drug in solution. A drug container, such as e.g. a bag or syringe, is usually provided with a medication label, indicating (at least) the identity of the drug and the concentration thereof. The necessary flow rate for infusion of drug from the drug container is calculated by the medical staff.

In other embodiments, the dose of the drug may be determined by means of a sensor device configured to measure a parameter of the patient, such as for example temperature, pulse, EKG, ECG or cell activity, wherein the sensor device may be connected to the control unit for automatic control of the drug dose. This way a more optimum dose may be infused into the patient.

The required dose rate for the drug is first calculated by dividing the dose, e.g. in μg, by the time interval, e.g. in minutes, to obtain the dose rate R in e.g. μg/min. To calculate the infusion rate (flow rate), the dose rate R (μg/min) is then divided by the concentration C, e.g. in μg/mL, to obtain the infusion rate as R/C in mL/min.

Sometimes it is desired or prescribed that the delivered dose rate should vary over time according to a predetermined protocol which is programmed in the control unit 10. For example, the infusion time may be divided into two or more intervals, each interval having a different (fixed) infusion rate to obtain a corresponding predetermined or prescribed dose rate.

When using the drug delivery system illustrated in FIG. 1, the calculated infusion rate is set on the pump 3 and the infusion is started. As liquid from the drug container 1 or 2 passes through the detection chamber the identity of the drug and its concentration are analyzed by the analytical detection unit 5 in conjunction with the control unit 10. For example, in a preferred embodiment, the analysis may be based on absorption spectrophotometry (IR, visible or UV range), and the optical spectra detected by the detection unit 5 are transferred to the control unit 10 which compares the spectra, i.e. chemical profile, with known data stored in the data storage 14. When the determined chemical profile is verified, the concentration of the drug is calculated from the magnitude of the spectral data transferred from the detection unit 5. If, on the other hand, the drug is not verified by the system, the control unit 10 immediately stops infusion by actuating the control valve 7. Provided that the drug has been verified to be that on the label of the drug container and that the drug concentration corresponds to the label concentration, the infusion of drug solution to the patient is allowed to proceed.

However, if the determined drug concentration deviates from the label concentration, the infusion of drug solution to the patient is still allowed to proceed, but the infusion rate is recalculated by the control unit 10 to a value maintaining the predetermined dose rate for the patient so that the predetermined drug dose has been obtained after the predetermined infusion time length. This recalculated infusion rate is set on the pump 3 by the control unit 10 via the control or feedback line 11.

The operations by the detection unit 5 are continuously repeated during the infusion process at suitable intervals, for example each 10, 15 or 30 seconds, but higher or lower detection frequencies may also be used, as found appropriate. For each detection cycle, a new dose rate calculation is performed based on the instantly measured concentration as well as the cumulative dose of drug infused up to that instant so that as far as possible the predetermined dose rate is maintained (in average) all the time.

For the case that the determined drug concentration is incorrect and far too high so that the patient would have obtained the total dose only during the first few seconds, the infusion is automatically stopped.

Figure 3:
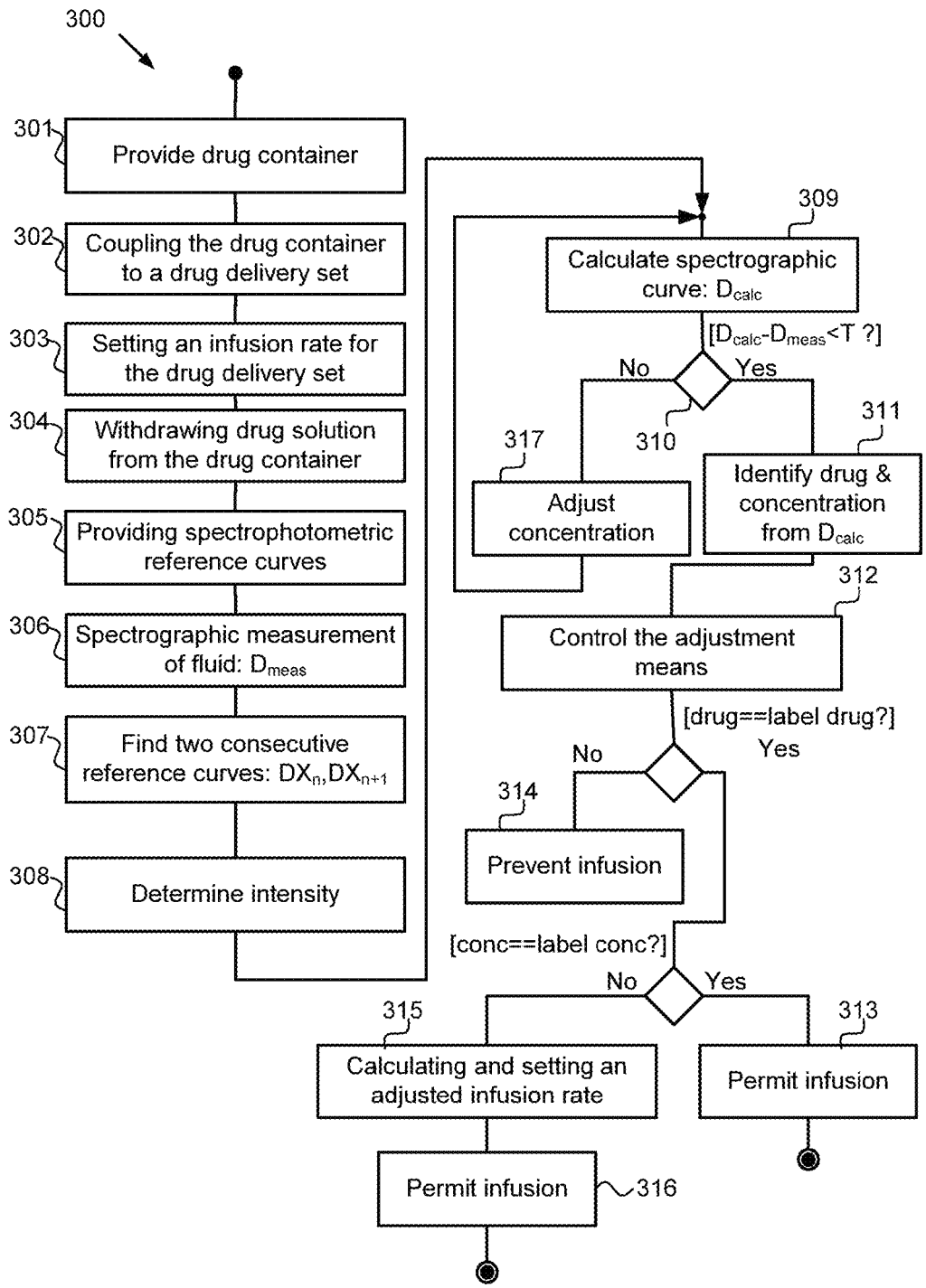
FIG. 3 is a flow diagram illustrating an embodiment of a method for drug infusion according to the present invention.

In FIG. 3 a method for administering a drug solution by infusion is disclosed in a flow diagram. The method comprising:

301: Providing a drug container with a label drug solution containing a label concentration of the drug.

302: Coupling the drug container to a drug delivery set for administration of drug solution to a patient by infusion via a fluid path, wherein the fluid path contains a detection chamber,

303: Based on the label concentration of the drug in the drug container, setting an infusion rate for the drug delivery set corresponding to a predetermined dose rate of the drug.

304: Withdrawing drug solution from the drug container through the detection chamber of the analytical detection means,

305: Providing spectrophotometric reference curves with different concentrations for the label drug to be identified. In a preferred embodiment the number of spectrophotometric reference curves is larger than X for each drug, or combination of drugs.

306: Performing a spectrophotometric measurement of the drug solution by means of the analytical detection means, wherein a measured spectrophotometric curve is obtained. The measured spectrophotometric curve comprises a set of wavelength intervals and for each wavelength interval is a corresponding absorbance factor recorded.

307: Finding two consecutive spectrophotometric reference curves from the provided spectrophotometric reference curves, such that the two consecutive spectrophotometric reference curves encompasses the measured spectrophotometric curve of the drug solution in a defined wavelength region. This means that the measured spectrophotometric curve is confined to the region between the two consecutive spectrophotometric reference curves in the defined wavelength region.

308: Determining the intensity for the measured spectrophotometric curve at a first wavelength. In a preferred embodiment the first wavelength corresponds to the wavelength where the difference between the two consecutive spectrophotometric curves is approximatively maximal. This way allows a good resolution in the measured intensity.

309: Calculating a calculated spectrophotometric curve of the fluid by means of the determined intensity using Beer-Lamberts law and the at least two consecutive spectrophotometric reference curves. In one embodiment the determined intensity is used to calculate a concentration of the drug, and the at least two spectrophotometric reference curves are used to determine the parameters in the Beer-Lamberts law. The calculated concentration and the determined parameters are then used in the Beer-Lamberts law for calculating the calculated spectrophotometric curve.

310: Determining if a difference between the calculated spectrophotometric curve and the measured spectrophotometric curve is smaller than a predetermined threshold.

311: Upon determining that the difference is smaller than the predetermined threshold, the drug is identified to be equal to the drug of the two consecutive reference curves, which is the label drug, and a determined concentration of the drug in the fluid is equal to the concentration of the drug in the calculated spectrophotometric curve.

312: Control the adjustment means to calculate and set the adjustment means to an adjusted infusion rate in order to maintain the predetermined dose rate when the drug concentration determined in the detection chamber deviates from the label concentration of the drug.

313: If the label drug is identified, and the determined drug concentration corresponds to the label concentration, permitting infusion of the drug solution at the set infusion rate.

314: If the label drug is not identified, preventing infusion of drug solution.

315: If the label drug is identified but the determined drug concentration does not correspond to the label drug concentration, calculating and setting an adjusted infusion rate for the drug delivery set which at least substantially will maintain the predetermined dose rate of the drug, and permitting infusion of the drug solution at the adjusted infusion rate.

Sometimes two or more drugs may be delivered simultaneously to the patient from e.g. three drug containers, as illustrated by the additional drug containers 1' and 1" and 2' and 2", respectively, which via pumps 3', 3", tubing parts 4', 4", detection units 5', 5" and tubing parts 6', 6" are connected, together with the tubing part 6, to a junction 9 which in turn is connected to the patient needle or cannula (not shown). Other ways of combining the liquid flows from the three tubing parts 6, 6', 6" are, of course, possible, e.g. by combining two tubing parts by a first junction and then adding the third tubing part via second junction.

In such a multiple drug delivery case, the infusion of drug from each drug container is analyzed separately and regulated as described above. While not seemingly feasible or practical today, future analytical methods may be capable of identifying and determining the concentrations of several drugs simultaneously, and it would then be possible to replace the three detection units 5, 5' and 5" by a single analytical detection unit, and the three detection chambers by a single detection chamber passed by the combined flows of drug solutions from the drug containers 1, 1' and 1" or 2, 2' or 2" (or combinations thereof).

In the system described above, flow of drug liquid from an infusion bag could alternatively take place by gravity, omitting the pump 3 and controlling the flow rate through a drip chamber and an adjustable valve which is controlled by the control unit 10. An example of such an automatically regulated drip chamber/valve device is described in U.S. Pat. No. 4,634,426.

In another embodiment, the dose rate of the infused drug may be adjusted in response to a physical parameter of the patient such as temperature, pulse, EKG/ECG information. The physical parameter may be measured with a sensor in contact with the patient and connected to the control unit. This way a closed control loop is formed that may provide an optimum drug infusion to the patient.

In another embodiment, the step of providing a drug container further comprises downloading patient data and a treatment protocol for veryfying the label drug and the label concentration. This way it is possible to verify that the correct drug container is connected to the drug delivery set. It is also possible to receive a desired dos rate profile from a central database containing treatment protocols and procedures.

In yet another embodiment, the method further comprises a step of storing information about the infusion upon completion of infusion. This way patient data can be updated and stored on a database.

As mentioned further above, the whole drug delivery system, except the drug container, could be provided in an infusion pump, for example of multi-channel type to permit simultaneous delivery of multiple drugs.

Optionally, a blood analysis system to measure the biological response to the actual dose rate may be integrated with the drug delivery system, and information obtained therefrom may be used as a variable in the dose rate setting.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A system for administering a drug solution by infusion, comprising: a drug container (1, 2) containing a label drug solution with a label concentration of a drug; a drug delivery set comprising a fluid conduit (4, 6) connected to the drug container (1, 2), means for connecting the fluid conduit (4, 6) to a patient (8), a detection chamber in the fluid conduit (4, 6) between the drug container (1, 2) and the patient connection means, and adjustment means for setting an infusion rate corresponding to a predetermined dose rate of the drug based on the label concentration, analytical detection means (5) for non-invasive determination in the detection chamber of the identity and concentration of the drug in fluid withdrawn from the drug container into to the fluid conduit, and means (7) for preventing infusion of drug solution from the drug container if the label drug is not identified, and a control unit comprising a processor (19) and a memory (20), said memory containing instructions executable by said processor whereby said processor is operative to: providing spectrophotometric reference curves with different concentrations for the label drug to be identified; performing a spectrophotometric measurement of the drug solution by means of the analytical detection means, wherein a measured spectrophotometric curve is obtained; finding two consecutive spectrophotometric reference curves from the provided spectrophotometric reference curves, such that the two consecutive spectrophotometric reference curves encompasses the measured spectrophotometric curve of the drug solution in a defined wavelength region; determining the intensity of the measured spectrophotometric curve at a first wavelength; calculating a calculated spectrophotometric curve of the fluid by means of the determined intensity and by using Beer-Lamberts law and the two consecutive spectrophotometric reference curves; determining if a difference between the calculated spectrophotometric curve and the measured spectrophotometric curve is smaller than a predetermined threshold; upon determining that the difference is smaller than the predetermined threshold, the drug is identified to be equal to the drug of the two consecutive reference curves, which is the label drug, and the concentration of the drug in the fluid is equal to the concentration of the drug in the calculated spectrophotometric curve; control the adjustment means and to calculate and set the adjustment means to an adjusted infusion rate in order to maintain the predetermined dose rate when the drug concentration in the fluid as determined in the detection chamber deviates from the label concentration of the drug.

2. The system according to claim 1, wherein said memory further containing instructions executable by said processor whereby said processor is further operative to select the first wavelength where a difference between the two consecutive spectrophotometric reference curves is maximum.

3. The system according to claim 1, wherein said memory further containing instructions executable by said processor whereby said processor is further operative to upon determining that the difference is larger than the predetermined threshold, adjust the concentration, and calculate the spectrophotometric curve using the adjusted concentration.

4. The system according to claim 1, wherein the analytical detection means is an absorbance spectrophotometer.

5. The system according to claim 1, wherein said memory further containing instructions executable by said processor whereby said processor is further operative to perform analysis of the drug concentration sequentially at a plurality of times during the infusion process, and at each time, based on the determined drug concentration and the cumulated infused dose of the drug, calculate a new infusion rate for the drug solution which at least substantially maintains the predetermined dose rate.

6. The system according to claim 1, wherein the drug delivery set comprises an infusion pump (3), the pump comprising the adjustment means for setting an infusion rate.

7. The system according to claim 6, wherein the detection chamber is provided in the infusion pump (3).

8. A method (300) of administering a drug solution by infusion, comprising: providing (301) a drug container with a label drug solution containing a label concentration of the drug, coupling (302) the drug container to a drug delivery set for administration of drug solution to a patient by infusion via a fluid path, wherein the fluid path contains a detection chamber, based on the label concentration of the drug in the drug container, setting an infusion rate (303) for the drug delivery set corresponding to a predetermined dose rate of the drug, withdrawing (304) drug solution from the drug container through the detection chamber, providing (305) spectrophotometric reference curves with different concentrations for the label drug to be identified; performing (306) a spectrophotometric measurement of the drug solution by means of an analytical detection means, wherein a measured spectrophotometric curve is obtained; finding (307) two consecutive spectrophotometric reference curves from the provided spectrophotometric reference curves, such that the two consecutive spectrophotometric reference curves encompasses the measured spectrophotometric curve of the drug solution in a defined wavelength region; determining (308) the intensity of the measured spectrophotometric curve at a first wavelength; calculating (309) a calculated spectrophotometric curve of the fluid by means of the determined intensity at the first wavelength and by using Beer-Lamberts law and the two consecutive spectrophotometric reference curves; determining (310) if a difference between the calculated spectrophotometric curve and the measured spectrophotometric curve is smaller than a predetermined threshold; upon determining that the difference is smaller than the predetermined threshold, the drug is identified (311) to be equal to the drug of the two consecutive reference curves, which is the label drug, and the concentration of the drug in the fluid is equal to the concentration of the drug in the calculated spectrophotometric curve; control (312) the adjustment means and to calculate and set the adjustment means to an adjusted infusion rate in order to maintain the predetermined dose rate when the drug concentration determined in the detection chamber deviates from the label concentration of the drug; if the label drug is identified, and the determined drug concentration corresponds to the label concentration, permitting infusion (313) of the drug solution at the set infusion rate, and if the label drug is not identified, preventing infusion (314) of drug solution, if the label drug is identified but the determined drug concentration does not correspond to the label drug concentration, calculating and setting (315) an adjusted infusion rate for the drug delivery set which at least substantially will maintain the predetermined dose rate of the drug, and permitting infusion (316) of the drug solution at the adjusted infusion rate.

9. The method according to claim 8, wherein said method further comprises selecting the first wavelength to a wavelength where a difference between the two consecutive spectrophotometric reference curves is maximal.

10. The method according to claim 8, wherein said method further comprises upon determining that the difference is larger than the predetermined threshold, adjust (317) the concentration used in the calculation of the calculated spectrophotometric curve, and calculate the spectrophotometric curve using the adjusted concentration.

11. The method according to claim 8, wherein said method further comprises performing analysis of the drug concentration sequentially at a plurality of times during the infusion process, and at each time, based on the determined drug concentration and the cumulated infused dose of the drug, calculate a new infusion rate for the drug solution which at least substantially maintains the predetermined dose rate.

12. The method according to claim 8, wherein the predetermined dose rate is varied according to a predetermined scheme with different fixed dose rates at two or more different intervals.

13. The method according to claim 8, wherein the step of providing a drug container (301) further comprises downloading patient data and a treatment protocol for verifying the label drug and the label concentration.

14. The method according to claim 8, further comprising a step of storing information about the infusion upon completion of infusion.

15. A computer readable storage medium storing computer program instructions which, when executed by a processor cause the processor to perform a method as set out in at least claim 8.

16. A signal carrying computer program instructions which, when executed by a processor cause the processor to perform a method as set out in at least claim 8.

17. The system of claim 6, wherein the infusion pump is a peristaltic pump or a syringe pump.

18. The system according to claim 7, wherein the analytical detection means (5) and at least part of the control unit (10) are provided in the infusion pump (3).

19. The system according to claim 2, wherein the drug delivery set comprises an infusion pump (3), the pump comprising the adjustment means for setting an infusion rate.

20. The system according to claim 3, wherein the drug delivery set comprises an infusion pump (3), the pump comprising the adjustment means for setting an infusion rate.

* * * * *